United States Patent [19]

Barcza

[11] 3,976,684
[45] Aug. 24, 1976

[54] 1-SUCCINOYL-2,4-DISUBSTITUTED-4b,5,6,7,8,8a,9,10-OCTAHYDRO-9-OXO-PHENANTHRENES AND COMPOSITIONS AND METHODS FOR TREATING LIPODEMIA

[75] Inventor: Sandor Barcza, West Orange, N.J.

[73] Assignee: Sandoz, Inc., E. Hanover, N.J.

[22] Filed: Apr. 4, 1975

[21] Appl. No.: 565,065

Related U.S. Application Data

[63] Continuation of Ser. No. 422,604, Dec. 6, 1973, abandoned.

[52] U.S. Cl. .................. 260/514.5; 260/590 FB; 424/317
[51] Int. Cl.² ............................................. C07C 65/20
[58] Field of Search .......... 260/514.5, 468.5, 520 D; 424/317; 422/604

[56] References Cited
UNITED STATES PATENTS

| | | | |
|---|---|---|---|
| 2,687,426 | 8/1954 | Hogg | 260/520 D |
| 3,497,532 | 2/1970 | Woodward | 260/520 D |
| 3,804,878 | 4/1974 | Bencye | 260/514.5 |

FOREIGN PATENTS OR APPLICATIONS

| | | | |
|---|---|---|---|
| 905,343 | 9/1962 | United Kingdom | 260/520 D |

OTHER PUBLICATIONS

Barnes et al., "J. Am. Chem. Soc.", vol. 74, pp. 5826–5828, (1952).

*Primary Examiner*—Norman Morgenstern
*Attorney, Agent, or Firm*—Gerald D. Sharkin; Robert S. Honor

[57] ABSTRACT

1-succinoyl-2,4-disubstituted-4b,5,6,7,8,8a,9,10-octahydro-9-oxo-phenanthrenes, e.g., 1-succinoyl-2,4-dimethoxy-4b,5,6,7,8,8a,9,10-octahydro-9-oxo-phenanthrene are prepared by treating a corresponding 2,4-dimethoxy-4b,5,6,7,8,8a,9,10-octahydro-9-oxo-phenanthrene with a Friedel Crafts catalyst in the presence of an organic solvent, and are useful as hypolipidemic agents.

4 Claims, No Drawings

1-SUCCINOYL-2,4-DISUBSTITUTED-4B,5,6,7,8,8A,9,10-OCTAHYDRO-9-OXO-PHENANTHRENES AND COMPOSITIONS AND METHODS FOR TREATING LIPODEMIA

This is a continuation of application Ser. No. 422,604, filed Dec. 6, 1973, now abandoned.

This invention relates to 1-succinoyl-2,4-substituted-4b,5,6,7,8,8a, 9,10-octahydro-9-oxo-phenanthrene derivatives, intermediates and processes for their preparation and their use as hypolipidemic agents.

The compounds of this invention may be represented by the following structural formula:

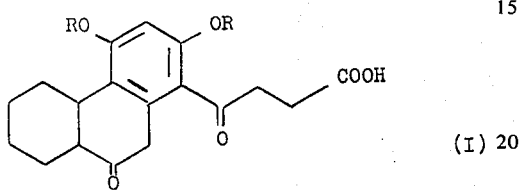

where
  R represents hydrogen, or lower alkyl, i.e. alkyl having 1 to 4 carbon atoms, e.g., methyl, ethyl, isopropyl and the like.

The compounds of formula (I) are prepared by the following reaction scheme:

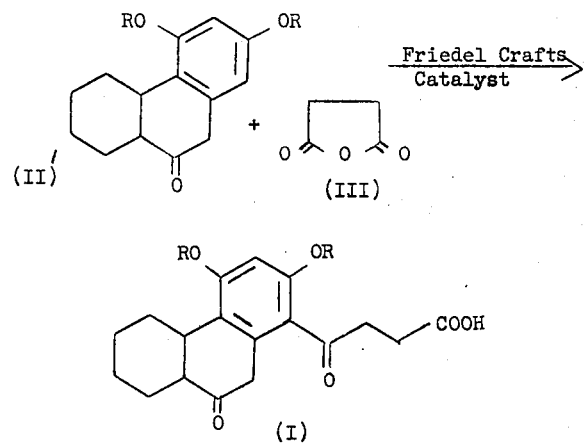

where
  R is a lower alkyl as defined above.

The compounds of formula (I) are prepared by treating a compound of the formula (II') with a compound of the formula (III) in the presence of a Friedel Crafts catalyst in an inert organic solvent, preferably under an inert atmosphere such as argon, neon, nitrogen and the like, preferably nitrogen. The particular Friedel Crafts catalyst employed is critical, and the reaction should be carried out in the presence of boron trifluoride, aluminum bromide, or aluminum chloride, the latter being especially preferred. The particular solvent employed is also critical, and the reaction should be carried out in the presence of nitrobenzene or a lower nitroalkane such as nitromethane, nitroethane and the like preferably nitromethane. The temperature of the reaction is not critical, but it is preferred that the reaction be carried out between about −50° to 40°C, preferably from about 0° to 30°C. The reaction is run from about 5 hours to 70 hours, preferably 10 to 24 hours. The product is recovered using conventional techniques e.g., quenching, extraction and crystallization.

The compounds of formula (II') may be prepared by the following reaction scheme:

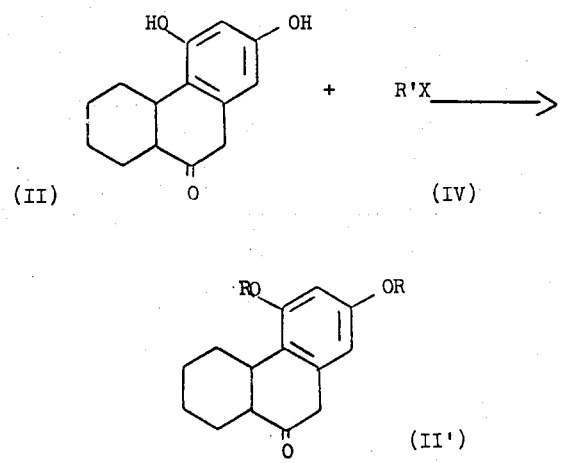

where
  X is a leaving group such as chloride, bromide, iodide or sulfate ion, preferably iodide or sulfate ion and
  R is lower alkyl as defined above.

The compounds of formula (II') are prepared by treating the compound of the formula (II) with a compound of the formula (IV) under an inert atmosphere such as argon, neon, nitrogen and the like, preferably nitrogen, in the presence of an inorganic acid binding agent such as sodium carbonate or potassium carbonate, or an organic binding agent, preferably potassium carbonate in the presence of a non-aqueous solvent such as dioxane, tetrahydrofuran or acetone, the latter being especially preferred. The temperature of the reaction is not critical, but it is preferred that the reaction be carried out between 50° and 150°C, especially the reflux temperature of the solvent. The reaction is run from about 20 to 50 hours, preferably 24 to 28 hours. The product is recovered using conventional techniques, e.g., recrystallization.

The compounds of formula (II) are prepared by the following reaction scheme:

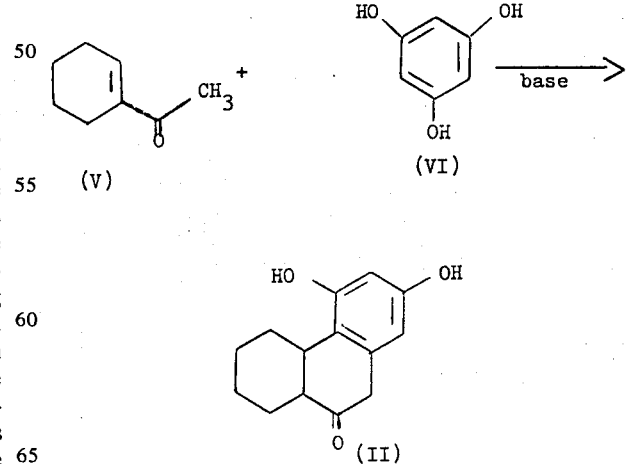

The compounds of formula (II) are prepared by treating 1-acetyl cyclohexene (V) with phloroglucinol (VI) under an inert atmosphere such as argon, neon, nitrogen and the like, preferably nitrogen, in the presence of both a strong base and an organic solvent. Suitable strong bases which may be employed include the alkali metal hydroxides, e.g., sodium hydroxide or potassium hydroxide, the latter being especially preferred. The reaction is carried out in the presence of an organic solvent such as the ethers of ethylene glycol, e.g., the methyl ether or ethyl ether, namely 2-methoxyethanol or 2-ethoxyethanol, preferably 2-methoxyethanol. The temperature of the reaction is not critical, but it is preferred that the reaction be run at temperatures from about 50° to 150°C, especially the reflux temperature of the solvent. The reaction is run from 1 to 40 hours, preferably 3 to 6 hours. The compounds of formula (II) are recovered using conventional techniques, e.g, recrystallization.

The compounds of formulae (III), (IV), (V) and (VI) are known and may be prepared by methods disclosed in the literature.

The compounds of formula (I) are useful because they possess pharmacological activity in animals as hypolipidemic agents, particularly as hyperlipoproteinemic agents as indicated by the fall of cholesterol and triglyceride levels in male albino Wistar rats weighing 110 to 130 g. initially. The rats are maintained on drug-free laboratory chow diets for seven days and then divided into groups of 8 to 10 animals. Each group, with the exception of the control, is then given orally 30 milligrams per kilogram of body weight per diem of the compound for 6 days. At the end of this period, the animals are anesthetized with sodium hexobarbital and bled from the carotid arteries. Serum or plasma samples are collected and 1.0 ml. samples of the serum are added to 9.0 ml. redistilled isopropanol. Two autoanalyzer cupsful of a mixture of zeolite-copper hydroxide and Lloydds reagent (Kessler, E., and Lederer, H., 1965, Technicon Symposium Mediad Inc., New York, (345-347) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g., a sterile injectable aqueous solution. The dosage will vary depending upon the mode of administration utilized and the particular compound employed.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 4.0 milligrams to about 250 milligrams per kilogram of animal body weight, preferably given in divided doses 2 to 4 times a day, or in sustained release form. For most large mammals, the total daily dosage is from about 250 milligrams to about 3000 milligrams. Dosage forms suitable for internal use comprise from about 62.5 to 1500 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg) |
| --- | --- |
| 1-succinoyl-2,4-dimethoxy-4b,5,6,7,8,8a,9,10-octahydro-9-oxo-phenanthrene | 150 |
| inert solid diluent (starch, lactose, kaolin). | 300 |

EXAMPLE 1

2,4-dihydroxy-4b,5,6,7,8,8a,9,10-octahydro-9-oxo-phenanthrene

To a flask equipped with a stirrer, dropping funnel, condenser and gas inlet tube maintained under a nitrogen atmosphere, there is added 50 g (0.89) moles of potassium hydroxide in one liter of 2-methoxyethanol. Stirring is initiated and 100 g(0.79mole) of anhydrous phloroglucinol is added in three portions, followed by the addition of 100 g (0.80 mole) of 1-acetyl-cyclohexene while maintaining the temperature at 50°C. The resulting solution is refluxed at 140°C for 4 hours. After cooling there is then added gradually 53.6 g. of acetic acid while obtaining a pH of approximately 7. The solvent is then removed in vacuo, and the residue is further heated in vacuo in a bath at 70°C, to obtain a viscous residue. The resulting residue is dissolved in ethyl acetate and water; washed twice with water, dried over anhydrous sodium sulfate, filtered and evaporated in vacuo to obtain a brown solid. The resulting solid is recrystallized from ethyl acetate/cyclohexane to give 2,4-dihydroxy-4b,5,6,7,8,8a,9,10-octahydro-9-oxo-phenanthrene. m.p. 220°-223°C.

EXAMPLE 2

2,4-dimethoxy-4b,5,6,7,8,8a,9,10-octahydro-9-oxo-phenanthrene.

To a flask equipped with a stirrer, dropping funnel, condenser, and gas inlet tube maintained under a nitrogen atmosphere, there is added 23.2 g (0.1 mole) of 2,4-dihydroxy-4b,5,6,7,8,8a,9,10-octahydro-9-oxo-phenanthrene, 20 g (0.15 mole) of dimethyl sulfate, 22 g (0.16 mole) of dry potassium carbonate and 500 ml of dry acetone, the resulting mixture is then refluxed with stirring overnight. The resulting suspension is cooled, 5 ml. of water is added and stirring is continued for an additional 5 minutes. The mixture is filtered, and the filtrate is concentrated to dryness. The resulting residue is recrystallized from acetone/methanol to give 2,4-dimethoxy-4b,5,6,7,8,8a,9,10-octahydro-9oxo-phenanthrene, m.p. 130°-131°C.

EXAMPLE 3

1-succinoyl-2,4-dimethoxy-4b,5,6,7,8,8a,9,10-octahydro-9-oxo-phenanthrene

To a flask equipped with stirrer, dropping funnel, condenser and gas inlet tube maintained under nitrogen atmosphere, there is added 10 g (0.07 mole) of aluminum chloride to 100 ml. of nitromethane preferably with a bath at room temperature. To the resulting solution there is then added 5.2 g (0.02 mole) of 2,4-dimethoxy-4b,5,6,7,8,8a,9,10-octahydro-9-oxo-phenanthrene and 3 g (0.03 mole) of succinic anhydride. The resulting mixture is then stirred overnight at room temperature. The residue is poured into ice water, extracted with ethylacetate, and dried with anhydrous magnesium sulfate and the ethylacetate solution is concentrated. The resulting residue is dissolved in a minimum amount of methanol, and an excess of saturated sodium bicarbonate is added, followed by water. The mixture is extracted with chloroform to remove any neutral ingredients. The aqueous phase is acidified with dilute hydrochloric acid and extracted wth ethyl acetate. The resulting solution is dried over anhydrous magnesium sulfate and concentrated to give a solid which is recrystallized from ethanol to give 1-succinoyl-2,4-dimethoxy-4b,5,6,7,8,8a,9,10-octahydro-9-oxo-phenanthrene, m.p. 168°–170°C.

What is claimed is:
1. A compound of the formula

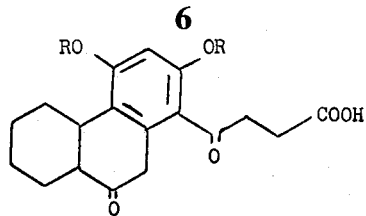

where
R represents hydrogen or lower alkyl having 1 to 4 carbon atoms.

2. The compound of claim 1 which is 1-succinoyl-2,4-dimethoxy-4b,5,6,7,8,8a,9,10-octahydro-9-oxo-phenanthrene.

3. A method of treating lipidemia which comprises administering to a mammal in need of said treatment a hypolipidemic effective amount of a compound of claim 1.

4. A pharmaceutical composition for treating lipidemia comprising a hypolipidemic effective amount of a compound of claim 1 and a pharmaceutically acceptable diluent or carrier therefor.

* * * * *